United States Patent [19]

Argoudelis et al.

[11] 3,988,314
[45] Oct. 26, 1976

[54] COMPOUND U-50,228, DERIVATIVES THEREOF, AND PROCESSES FOR PREPARATION

[75] Inventors: Alexander D. Argoudelis, Portage; Stephen A. Mizsak, Kalamazoo, both of Mich.

[73] Assignee: The Upjohn Company, Kalamazoo, Mich.

[22] Filed: Oct. 10, 1975

[21] Appl. No.: 621,306

[52] U.S. Cl. .................................. 536/1; 195/80 R; 424/180; 536/18
[51] Int. Cl.$^2$ .......................................... C07H 3/02
[58] Field of Search .......... 260/209, 211.5 R, 209 R

[56] References Cited
UNITED STATES PATENTS

| | | | |
|---|---|---|---|
| 3,755,293 | 8/1973 | Shirato et al. | 260/209 R |
| 3,907,643 | 9/1975 | DeBoer et al. | 260/211.5 R |
| 3,907,779 | 9/1975 | DeBoer et al. | 260/211.5 R |

OTHER PUBLICATIONS

Michelson, "The Chem. of Nucleosides and Nucleotides," Academic Press, New York, N.Y. 1963, pp. 12–14.

Cohn, "J. Biol. Chem." vol. 235, 1960, pp. 1488–1498.

Scannell et al. et al., "Biochim. et. Biophys. Acta." vol. 32, 1959, pp. 409–412.

*Primary Examiner*—Johnnie R. Brown
*Attorney, Agent, or Firm*—Roman Saliwanchik

[57] ABSTRACT

New antiviral agent U-50,228 and derivatives thereof, produced by the controlled fermentation of the known microorganism *Streptomyces platensis* var. *clarensis* var nova, NRRL 8035. This antiviral agent and its derivatives are active against DNA-viruses, for example, the Herpes virus and, thus, can be used to control such virus where its presence is not desired. For example, U-50,228 and its derivatives can be used to swab laboratory benches and equipment in a virology laboratory to eliminate the presence of Herpes virus.

7 Claims, No Drawings

COMPOUND U-50,228, DERIVATIVES THEREOF, AND PROCESSES FOR PREPARATION

BACKGROUND OF THE INVENTION

The antiviral agent of the subject invention is produced concomitantly with antibiotic U-44,590. The fermentation conditions and characteristics of the producing microorganism are disclosed in U.S. Pat. Nos. 3,907,643 and 3,907,779. There is no disclosure of the production of antiviral U-50,228 in these patents.

U-50,228 has been determined through structural studies to be 1-methylpseudouridine. Pseudouridine is a known compound having been isolated in 1958 from hydrolysates of "soluble ribonucleic acids". (The Chemistry of Nucleosides and Nucleotides by A. M. Michelson, Academic Press, New York 1963, p. 12).

In the course of structural studies with pseudouridine, Waldo E. Cohn, *J. Biol. Chem.*, 235, 1488 (1960) reacted pseudouridine with diazomethane. The reaction mixture was characterized by paper chromatography; there was no isolation of products. On the basis of $R_f$ values and UV, tentative structures for the three compounds observed in the papergrams were assigned. One of these tentative structures was for 1-methylpseudouridine. Similarly, J. P. Scannell, A. M. Crestfield and F. W. Allen reported in *Biochim. et. Biophys. Acta*, 32, 409 (1959) that they methylated pseudouridine using dimethylsulfate. A mixture of six "methylated pseudouridine derivatives" was resolved by paper chromatography. By comparison with the methylation reaction products obtained from uridine and uracil the authors concluded that two NH-groups in pseudouridine are "free" and that the ribose moiety is attached to carbon. As disclosed above, the compound of the subject invention was not isolated and, therefore, not characterized in any of the known prior art publications.

BRIEF SUMMARY OF THE INVENTION

The novel antiviral agent of the invention, U-50,228 is obtained by culturing *Streptomyces platensis* var. *clarensis*, NRRL 8035, in an aqueous nutrient medium under aerobic conditions. Produced concomitantly with U-50,228 is the known antibiotic U-44,590. These chemical compounds are readily separated from each other during the purification process as described herein.

Antiviral U-50,228 has been characterized as 1-methylpseudouridine having the following structure:

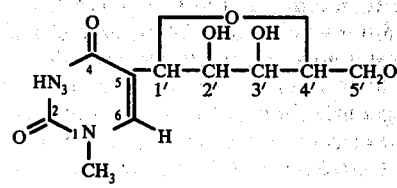

U-50,228 and its acylates and phosphate esters are active against DNA-viruses, for example, Herpes virus. U-50,228 and its triacetate have been found inactive against several Gram-positive and Gram-negative bacteria on an in vitro test. Because of the antiviral properties of U-50,228 and its derivatives, as disclosed herein, these agents are useful to control DNA viruses in various environments, for example, virology laboratories.

DETAILED DESCRIPTION OF THE INVENTION

Chemical and Physical Properties of U-50,228

Elemental Analysis

Calcd. for $C_{10}H_{14}N_2O_6$:

Molecular Weight: The molecular weight was obtained by high resolution mass spectrometry on the trimethylsilyl derivative of U-50,228, $C_{10}H_{10}N_2O_6[Si(CH_3)_3]_4$. Calcd., 546.2433; Found, 546.2406.

Melting Point: 181°–184° C.

Optical Rotation: $[\alpha]_D^{25} = -25°$ (50% aqueous ethanol)

Solubilities: Highly soluble in water, methanol, ethanol; slightly soluble in acetone, and relatively insoluble in higher ketones, ethyl acetate, benzene, and saturated or chlorinated hydrocarbon solvents.

Infrared Absorption Spectra: U-50,228 has a characteristic infrared absorption spectrum when suspended in a mineral oil mull. Peaks are observed at the following wave lengths expressed in reciprocal centimeters:

| Band Frequency (Wave Numbers) | Intensity |
| --- | --- |
| 3390 | S |
| 3355 | S |
| 3200 sh | W |
| 3060 | W |
| 3040 | W |
| 2950 N | S |
| 2930 N | S |
| 2860 N | S |
| 1720 | M |
| 1692 sh | S |
| 1672 | S |
| 1649 | S |
| 1515 | W |
| 1485 | M |
| 1468 N | M |
| 1432 | W |
| 1412 | M |
| 1378 N | M |
| 1340 | M |
| 1312 | W |
| 1295 | W |
| 1267 | W |
| 1238 | W |
| 1222 | W |
| 1210 | W |
| 1195 | W |
| 1152 | W |
| 1135 | W |
| 1117 | M |
| 1100 | S |
| 1085 | M |
| 1073 | W |
| 1048 | M |
| 1025 | M |
| 983 | W |
| 949 | W |
| 935 | W |
| 918 | W |
| 875 | W |
| 850 | W |
| 795 | W |
| 785 | M |
| 770 | W |
| 760 | W |
| 739 | W |
| 712 | W |

Note: sh means a shoulder band and N means mineral oil.

U-50,228 also has a characteristic infrared absorption spectrum when placed in a KBr disc. Peaks are observed at the following wave lengths expressed in reciprocal centimeters:

| Band Frequency (Wave Numbers) | | Intensity |
|---|---|---|
| 3400 | | S |
| 3350 | sh | S |
| 3080 | | M |
| 3060 | | M |
| 3040 | | M |
| 2950 | | M |
| 2930 | | M |
| 2910 | | M |
| 2900 | | W |
| 2860 | | W |
| 1718 | sh | M |
| 1685 | sh | S |
| 1672 | | S |
| 1648 | | S |
| 1515 | | W |
| 1485 | | M |
| 1465 | | W |
| 1430 | | W |
| 1410 | | W |
| 1378 | | W |
| 1342 | | M |
| 1312 | | W |
| 1295 | | W |
| 1266 | | W |
| 1238 | | W |
| 1221 | | W |
| 1210 | | W |
| 1195 | | W |
| 1150 | sh | W |
| 1135 | | W |
| 1115 | | M |
| 1098 | | M |
| 1082 | | W |
| 1070 | | W |
| 1048 | | M |
| 1022 | | M |
| 890 | | W |
| 958 | | W |
| 933 | | W |
| 916 | | W |
| 872 | | W |
| 850 | | W |
| 793 | | W |
| 785 | | W |
| 769 | | W |
| 758 | | W |
| 738 | | W |
| 710 | | W |

Infrared band intensities, throughout this disclosure, are indicated as S, M, and W respectively and are approximated in terms of the backgrounds in the vicinity of the bands. An S band is of the same order of intensity as the strongest in the spectrum; M bands are between ⅓ and ⅔ as intense as the strongest band; and, W bands are less than ⅓ as intense as the strongest band. These estimates are made on the basis of a percent transmission scale.

Ultraviolet Absorption Spectra

| Solvent | λ Max (mµ) | a |
|---|---|---|
| Water | 209 | 37 |
| | 270 | 35.2 |
| Water pH 1.0 | 209 (sh) | 36.6 |
| | 270 | 34.2 |
| Water pH 11.0 | 267 | 24 |

The following is considered to be the structure of U-50,228.

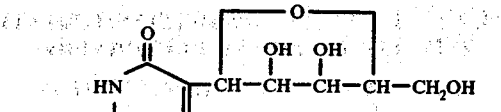

Thus, U-50,228 can be referred to by the trivial name 1-methylpseudouridine.

Antiviral Activity Of U-50,228

Antiviral U-50,228 is effective against Herpes simplex virus −1 in vitro at a concentration of 100 µg/ml.

THE MICROORGANISM

The microorganism used for the production of U-50,228 is *Streptomyces platensis* var. *clarensis*, NRRL 8035. A subculture of this microorganism can be obtained from the permanent collection of the Northern Regional Research Laboratory, U.S. Department of Agriculture, Peoria, Illinois, U.S.A. This is a known microorganism which has previously been disclosed as a producer of the antibiotic U-44,590 (See U.S. Pat. No. 3,907,643). Though a subculture of this microorganism is freely available from the depository by request made thereto, it should be understood that this availability of the culture does not constitute a license to practice the subject invention in derogation of patent rights granted with the subject instrument by governmental action.

The new compound of the invention is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of the compound of the invention can be effected at any temperature conducive to satisfactory growth of the microorganism, for example, between about 18° and 40° C., and preferably between about 20° and 32° C. Ordinarily, optimum production of the compound is obtained in about 5 to 15 days. The medium normally remains neutral during the fermentation. The final pH is dependent, in part, on the buffers present, if any and in part on the initial pH of the culture medium.

When growth is carried out in large vessels and tanks, it is preferable to use the vegetative form, rather than the spore form, of the microorganism for inoculation to avoid a pronounced lag in the production of the new compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the new compound, so long as a good growth of the microorganism is obtained.

A variety of procedures can be employed in the isolation and purification of the compound of the subject invention, for example, solvent extraction, partition chromatography, silica gel chromatography, liquid-liquid distribution in a Craig apparatus, absorption on resins, and crystallization from solvents.

In a preferred recovery process the compound of the subject invention is recovered from the culture medium by separation of the mycelia and undissolved solids by conventional means, such as by filtration or centrifugation. The antibiotic is recovered from the filtered or centrifuged broth by adsorption on activated carbon. The activated carbon is then washed with water to remove some impurities. This is followed by elutions with acetone: water solutions which remove the antibiotic from the activated carbon. The acetone in the eluates is removed, advantageously by evaporation, and the remaining aqueous residue is lyophilized to afford a crude preparation containing a mixture of antibiotic U-44,590 and antiviral U-50,228.

Antiviral U-50,228 can be separated from antibiotic U-44,590 and isolated in a relatively pure form by further purification procedures. In one procedure, the crude preparation containing a mixture of antibiotic U-44,590 and U-50,228 can be purified by counter double current distribution using a solvent system consisting of, for example, 1-butanol-water (1:1), followed by silica gel chromatography using a solvent system consisting of, for example, ethylacetate-methanol (6:1 v/v). Another purification procedure for resolving a mixture of U-50,228 and U-44,590 involves the use of a series of silica gel chromatographies using first a solvent system consisting of, for example, methanol:-chloroform (1:1 v/v), and then ethyl acetate: methanol (6:1 v/v). This procedure yields a highly purified mixture of U-50,228 and antibiotic U-44,590. The mixture can then be resolved by acetylation. Purification of acetylated U-50,228 can be accomplished by silica gel chromatography using a solvent system consisting of, for example, ethyl acetate:Skellysolve B (isomeric hexanes): methanol (60:30:1 v/v). Deacetylation yields a relatively pure preparation of U-50,228.

Antiviral U-50,228 can be acylated with any readily available acylating agent to give acylated U-50,228. This acylated U-50,228 product can then be deacylated by methods well known in the art to yield a purer preparation of U-50,228. Readily available acylating agents which can be used to acylate U-50,228, and which are within the scope of this invention, are as disclosed in U.S. Pat. No. 3,426,012, Columns 5 and 6.

The 5'-monoesters of U-50,228 can be formed by standard procedures using a minimum amount of acylating agent.

The 2',3'-diesters can be formed by tritylating U-50,228 to give the 5'-trityl derivative, acylating this compound with the desired acylating agent selected from those above, to give the 2',3'-diester 5'-trityl derivative, which then can be converted to the 2',3'-diester by removal of the trityl group. The tritylation procedure disclosed in U.S. Pat. No. 3,426,012, Columns 4 and 5, or other standard tritylation procedures can be employed. The trityl group can be removed by using the procedure disclosed in U.S. 3,426,012, in Column 6.

The 5'-phosphate of U-50,228 can be prepared by procedures as disclosed in the work of D. Mitsunobu, K. Kato, and J. Kimura, *J. Amer. Chem. Soc.*, 91, 6510 (1969). This compound can be used for the same purposes as U-50,228.

The compounds, described above, being the derivatives of U-50,228 which are within the scope of the subject invention, can be shown by the following structural formula

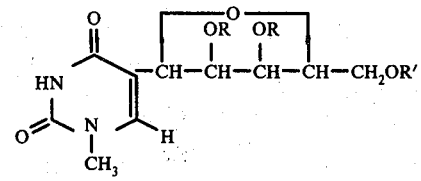

wherein R and R' are selected from the group consisting of a carboxylic acid acyl radical of from 2 to 18 carbon atoms, inclusive; or a halo-, nitro-, hydroxy-, amino-, cyano-, thiocyano-, and lower alkoxy-substituted hydrocarbon carboxylic acid acyl radical of from 2 to 18 carbon atoms, inclusive; R is hydrogen and R' is as defined above or phosphate; or R' is hydrogen and R is a carboxylic acid acyl radical of from 2 to 18 carbon atoms, inclusive; or a halo-, nitro-, hydroxy-, amino-, cyano-, thiocyano-, and lower alkoxy-substituted hydrocarbon carboxylic acid acyl radical of from 2 to 18 carbon atoms, inclusive, or phosphate.

Since antiviral U-50,228 is active against DNA viruses, it can be used in various environments, for example, virology laboratories, to control these viruses by swabbing laboratory benches and equipment. The derivatives of U-50,228, as described above, can be used for the same purposes as U-50,228.

The following examples are illustrative of the process and products of the present invention but are not to be construed as limiting. All percentages are by weight and solvent mixture proportions are by volume unless otherwise noted.

EXAMPLE 1

Part A. Fermentation

A soil stock of *Streptomyces platensis* var. *clarensis*, NRRL 8035, is used to inoculate a series of 500-ml Erlenmeyer flasks, each containing 100 ml of sterile seed medium consisting of the following ingredients:

| | |
|---|---|
| Glucose monohydrate | 10 Gm/l |
| Bacto Peptone (Difco) | 10 Gm/l |

| | |
|---|---|
| Bacto Yeast Extract (Difco) | 2.5 Gm/l |
| Deionized water | Balance |

The flasks are grown for 2 days at 28° C. on a Gump rotary shaker operating at 250 r.p.m.

Seed inoculum, described above, is used to inoculate a series of 500 ml Erlenmeyer flasks each containing 100 ml of sterile fermentation medium. The inoculation rate is 5 ml of seed inoculum per 100 ml of fermentation medium. The fermentation medium consists of the following ingredients:

| | |
|---|---|
| Brer Rabbit Molasses (RJR Foods Inc., N.Y., N.Y. 10017) | 20 ml |
| Yeast Extract (Difco) Detroit, Michigan | 1 Gm/l |
| Glucose monohydrate | 10 Gm/l |
| Dextrin (Corn Products Co. International Inc., International Plaza, Englewood Cliffs, New Jersey 07632 | 10 Gm/l |
| Proteose Peptone No. 3 (Difco) | 10 Gm/l |
| Tap water q.s. | Balance |

The presterilization pH is 7.0. The inoculated fermentation flasks are incubated at a temperature of 28° C. on a Gump rotary shaker operating at 250 r.p.m. with a 2½ inch stroke. Ucon antifoam (a synthetic defoamer supplied by Union Carbide, N.Y., N.Y.) is used if needed. Harvest is usually after 5 to 12 days of fermentation.

The production of U-50,228 is followed by determining the antibiotic titer on an agar plate disc assay using the bacterium *Klebsiella pneumoniae*. This assay determines the production of U-44,590. High titers of U-44,590 is indicative of high titers of U-50,228. This bacterium is inoculated into the assay agar (Streptomycin Assay Agar, BBL, Cockeysville, Maryland 21030) of the following composition:

| | |
|---|---|
| Beef Extract | 1.5 Gm/l |
| Yeast Extract | 3.0 Gm/l |
| Gelysate Peptone, supplied by Baltimore Biological Labs. | 6.0 Gm/l |
| Agar | 15.0 Gm/l |
| Deionized water adjust pH to 7.9. | Balance |

Sterilize at 121° C. (15 pounds steam pressure) for 15 minutes.

Phosphate buffer (0.1N pH 6.0) is used as the diluent. The agar plates are incubated at 37° C. for 16–18 hours. Presence of antibiotic U-44,590 and therefore of the antiviral U-50,228 is evidenced by the zone of inhibition around a paper disc to which a fermentation sample was previously applied. The diameter of the zone of inhibition reflects the potency of the antibiotic sample. Thus, a 20 mm zone of inhibition using a 12.7 mm paper disc to which 0.08 ml of antibiotic sample has been applied is expressed as one bio unit per ml (1 BU/ml).

Part B. Recovery

Whole fermentation beer (ca 1600 ml assaying 5 BU/ml against *K. pneumoniae*), obtained as described above, is filtered using diatomaceous earth as a filter aid. The filter cake is washed with water. The clear beer and wash (1800 ml) is then passed through an activated carbon column. The column measures 2.8 × 44 cm and contains 126 grams of activated carbon. The carbon column is washed with 1750 ml water and the wash is discarded. The column is then washed with 1 liter each of 1%, 2% and 5% acetone:water concentration. These eluates are also discarded. The column is then eluted with 1 liter each of a 10%, 25% and 50% acetone:water concentration. These eluates, which contain antibiotic U-44,590 and antiviral U-50,228 are pooled and the acetone is removed on a rotatory evaporator at 30° C./15 mm Hg. The resulting acetone-free preparation is shell-frozen to an aqueous residue and then lyophilized, yield, 3.55 grams assaying 2 BU/mg of U-44,590 against *K. pneumoniae*. This preparation, which contains a mixture of U-44,590 and U-50,228, is labeled for convenience as Solid A.

Part C. Purification

1. Counter Double Current Distribution

A preparation of a mixture of antibiotic U-44,590 and U-50,228, obtained as described above in Part B, is subjected to counter double current distribution using a solvent system consisting of 1-butanol-water (1:1). The starting material, Solid A, is put in tubes 24–27 on the side where the lower phase of the system enters the distribution machine. The following transfers are run:
1. 22 transfers without collecting fractions
2. 50 transfers collecting the upper phase only
3. 100 transfers collecting both phases.

The distribution is analyzed for bioactivity using *K. pneumoniae* (indicative of the presence of U-44,590) as the assay organism. Fractions are analyzed on thin layer chromatography (tlc) which is conducted on silica gel plates using the solvent system ethyl acetate-methanol (6:1 v/v). Zones of the antibiotic are detected by spraying the plates with $IO_4^-/MnO_4^-$ spray, and with 50% aq. $H_2SO_4$ followed by heating at 110° C. for ca 10 minutes. The $R_f$ of U-44,590 is 0.51, and the $R_f$ of U-50,228 is 0.45 on the above solvent system. Pools of fractions containing U-44,590 and U-50,228 are made on the basis of the tlc results. Each pool is concentrated to dryness to give the following preparations:

Pool I: Lower collector 10–45, Prep. 3.1, 14.0 g
Pool II: Lower collector 46–99, Prep. 3.2, 5.59 g
Pool III: Lower machine 50–0, Prep. 3.3, 3.58 g
Pool IV: Upper collector 0–20, Prep. 9.1, 8.57 g Preparation 3.1 which contains both U-50,228 and U-44,590 is purified further by silica gel chromatography, as described below.

2. Silica Gel Chromatography

The column is prepared from 1.8 kg of silica gel (Merck - Darmstadt Art 7034) packed in ethyl acetatemethanol (6:1 v/v). The starting material, Prep. 3.1, 13.5 g. obtained as described above, is dissolved in 100 ml of methanol. The solution is then mixed with 100 g of silica gel and 500 ml of ethyl acetate. The mixture is concentrated to dryness in vacuo. The powder obtained is added on the top of the column. The column is eluted with the solvent and fractions (20 ml) are collected. Fractions are analyzed by tlc and bioactivity against *K. pneumoniae*, both as described above. The following pools are made:

Pool I — fractions 310–350
Pool II — fractions 365–385
Pool III — fractions 400–420

Pool IV — fractions 421–540
Pool V — fractions 565–615
Pool VI — fractions 616–670
Pool VII — fractions 671–820
Pool VIII — fractions 821–1100.

The following preparations are obtained by concentrating the above pools to dryness. The residues obtained are dissolved in a minimum amount of methanol and this solution is mixed with ether. The resulting precipitated materials are isolated by filtration and dried.

From Pool I — Prep. 1.1, 5 mg
From Pool II — Prep. 1.2, 5 mg
From Pool III — Prep. 1.3, 5 mg
From Pool IV — Prep. 1.4, 92.3 mg
From Pool V — Prep. 1.5, 184.7 mg
From Pool VI — Prep. 1.6, 189.5 mg
From Pool VII — Prep. 1.7, 307.8 mg
From Pool VIII — Prep. 1.8, 414 mg Prep. 1.7 contains relatively pure antiviral U-50,228.

EXAMPLE 2

Alternate Purification

A — First Silica Gel Chromatography

A silica gel column is prepared from 420 g of silica gel (Merck - Darmstadt Art 7734) packed in methanol:chloroform (1:1 v/v). The column measures 3.8 × 88 mm. Solid A, obtained as described above in Example 1, Part B, is added on the top of the column and the column is then eluted with methanol:chloroform (1:1 v/v). Active fractions, as determined by the above described *K. pneumoniae* assay, are pooled and the solvent is removed from said pooled fractions by the use of a rotary evaporator at 30° C./15 mmHg; yield, 830 mg assaying 7.5 BU/mg and containing both U-50,228 and U-44,590.

B — Second Silica Gel Chromatography

A preparation of the mixture of U-50,228 and U-44,590, obtained as described above, is subjected to chromatography on silica gel using the solvent system ethyl acetate: methanol (6:1 v/v) to give a purer preparation containing U-44,590 and U-50,228. Fractions from the column containing U-44,590 and U-50,228 are combined and concentrated to dryness in vacuo to give a syrup. Crystalline U-44,590 is removed by crystallization from ethyl acetate and the mother liquors are concentrated to dryness in vacuo to give a syrup. This material is used as the starting material for the acetylation described below.

C — Acetylation Of A Mixture Of U-50,228 and U-44,590

A mixture of U-44,590 and U-50,228 (42.3 g) is dissolved in 350 ml of acetic anhydride and 15 ml pyridine. The solution is stirred and heated at 75° for 72 hours. The reaction mixture is then concentrated to dryness in vacuo. The resulting residue is dissolved in 200 ml of boiling ethyl acetate and the solution is clarified by filtration. The solution is allowed to stand at room temperature for 12 hours. Crystalline U-44,590 diacetate, ca 31.3 g is isolated by filtration. The mother liquors containing U-50,228 triacetate are concentrated to dryness to give Prep. 7.1, 20.3 g. Purification of this material is obtained by the silica gel chromatography described below.

D — Silica Gel Chromatography of U-50,228 Triacetate

The column is prepared from 1.8 kg of silica gel (Merck - Darmstadt Art 7034) packed in ethyl acetate-Skellysolve B-methanol (60:30:1 v/v). The starting material, Prep. 7.1 (20.3 g) is dissolved in ethyl acetate-methanol (60:1 v/v) and silica gel, 100 g, and Skellysolve B, 30 ml are added. The mixture is concentrated to dryness. The powder obtained is added on the top of the column. The column is then eluted with the above solvent system. Fractions (20 ml) are collected at a rate of 4 ml/min. and analyzed by tlc, as described above.

Fractions 1-839 are discarded. The following pools are made. Each pool is concentrated to dryness to yield the indicated preparations:

Pool I — Fractions 840–1080, Prep. 97.1, 0.46 g
Pool II — Fractions 1120–1250, Prep. 97.2, 0.17 g
Pool III — Fractions 1260–1480, Prep. 97.3, 6.2 g
Pool IV — Fractions 1481–1730, Prep. 97.4, 1.3 g Prep. 97.3 contains relatively pure crystalline colorless U-50,228 triacetate which is henceforth designated U-50,227 and has the following characteristics:

Chemical and Physical Properties of U-50,227

Elemental Analysis

Calcd. for $C_{16}H_{20}N_2O_9$: C, 50.00; H, 5.21; N, 7.30; O, 37.50.

Molecular Weight: 384 (high resolution mass spectrometry)

Melting Point: 117°–120° C.

Optical Rotation: $[\alpha]_D^{25} = +9°$ (c, 1, $CHCl_3$)

Solubilities: Highly soluble in alcohols, ketones, esters, chloroform, and methylene chloride; relatively insoluble in water and saturated hydrocarbon solvents.

Infrared Absorption Spectra: U-50,227 has a characteristic infrared absorption spectrum when suspended in a mineral oil mull. Peaks are observed at the following wave lengths expressed in reciprocal centimeters:

| Band Frequency (Wave Numbers) | Intensity |
| --- | --- |
| 3460 | W |
| 3160 | M |
| 3090 | W |
| 3030 | M |
| 3000 | W |
| 2950 N | S |
| 2920 N | S |
| 2850 N | S |
| 2800 | W |
| 1745 | S |
| 1722 | S |
| 1702 | S |
| 1668 | S |
| 1518 | W |
| 1465 N | M |
| 1425 | M |
| 1418 | M |
| 1398 | M |
| 1380 | M |
| 1375 N | M |
| 1368 | M |
| 1342 | W |
| 1322 | M |
| 1305 | M |
| 1275 | M |
| 1253 | S |
| 1222 | S |
| 1170 | W |
| 1138 | W |
| 1108 | M |
| 1098 | M |
| 1068 | M |
| 1043 | M |

-continued

| Band Frequency (Wave Numbers) | Intensity |
|---|---|
| 1020 | M |
| 998 | W |
| 983 | W |
| 955 | M |
| 938 | W |
| 918 | W |
| 908 | W |
| 882 | W |
| 850 | M |
| 788 | W |
| 780 | W |
| 759 | W |
| 750 | W |
| 715 N | W |
| 665 | W |

U-50,227 also has a characteristic infrared absorption spectrum when placed in a KBr disc. Peaks are observed at the following wave lengths expressed in reciprocal centimeters:

| Band Frequency (Wave Numbers) | Intensity |
|---|---|
| 3450 | M |
| 3170 | W |
| 3100 | W |
| 3030 | W |
| 2960 | W |
| 2800 | W |
| 1745 | S |
| 1722 | S |
| 1702 | S |
| 1670 | S |
| 1518 | W |
| 1485 | M |
| 1462 | M |
| 1440 | W |
| 1425 | W |
| 1417 | W |
| 1398 | M |
| 1380 | M |
| 1372 | M |
| 1340 | W |
| 1322 | M |
| 1305 | M |
| 1252 | S |
| 1233 | S |
| 1222 | S |
| 1168 | W |
| 1108 | M |
| 1098 | M |
| 1068 | M |
| 1043 | M |
| 1018 | W |
| 983 | W |
| 955 | W |
| 938 | W |
| 915 | W |
| 905 | W |
| 882 | W |
| 850 | W |
| 788 | W |
| 780 | W |
| 758 | W |
| 750 | W |
| 715 | W |
| 665 | W |

Ultraviolet Absorption Spectrum

| Solvent | λ Max (mμ) | a |
|---|---|---|
| 95 % ethanol | 269 | 24 |

Antiviral U-50,227 is the triacetate of U-50,228.

Antiviral Activity Of U-50,227

Antiviral U-50,227 is effective against Herpes simplex virus—1 in vitro at a concentration of 100 μg/ml.

EXAMPLE 3

Deacetylation Of U-50,227 to U-50,228

Three grams of crystalline U-50,227, prepared as described in Example 2, is dissolved in 40 ml of absolute methanol. Concentrated ammonium hydroxide (0.22 ml) is added to the methanolic solution. The mixture is allowed to stand at room temperature for 48 hours; it is then concentrated to dryness to give a Preparation of U-50,228 labeled 153.1, 3.0 g, which is purified by the silica gel chromatography described below.

EXAMPLE 4

Silica Gel Chromatography of U-50,228 Preparation

The column is prepared from 450 g of silica gel (Merck - Darmstadt Art 7034) packed in ethyl acetate-methanol (6:1 v/v). The starting material, Prep. 153.1 3.0 g, obtained as described in Example 3, is dissolved in 15 ml of methanol and this solution is mixed with 25 g of silica gel and 80 ml of ethyl acetate. The mixture is concentrated to dryness. The powder obtained is added on top of the column. The column is eluted with the above solvent, and the fractions analyzed by tlc. Fractions 140–250 containing U-50,228 are combined and concentrated to a volum of ca 100 ml. Relatively pure crystalline U-50,228 (600 mg) is isolated by filtration.

We claim:

1. Pure U-50,228, characterizable by the following structure:

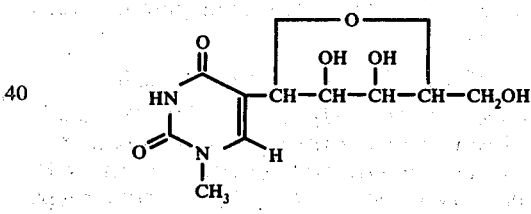

2. A compound of the formula:

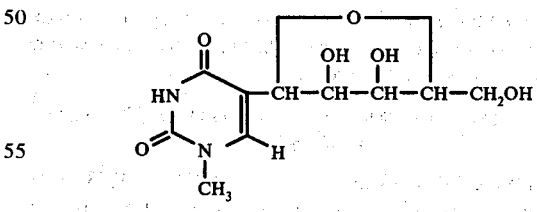

wherein R and R' are selected from the group consisting of a carboxylic acid acyl of from 2 to 18 carbon atoms, inclusive; or a halo-, nitro-, hydroxy-, amino-, cyano-, thiocyano-, and lower alkoxy-substituted hydrocarbon carboxylic acid acyl of from 2 to 18 carbon atoms, inclusive; R is hydrogen and R' is as defined above or phosphate; or R' is hydrogen and R is a carboxylic acid acyl of from 2 to 18 carbon atoms, inclusive; or a halo-, nitro-, hydroxy-, amino-, cyano-, thiocyano-, and lower alkoxy-substituted hydrocarbon carboxylic acid acyl of from 2 to 18 carbon atoms, inclusive, or phosphate.

3. U-50,227, a compound according to claim 2, wherein R and R' are acetyl.

4. A process for isolating pure U-50,228 from a preparation containing a mixture of U-50,228 and U-44,590, which comprises:
 a. subjecting a mixture of antibiotic U-44,590 and U-50,228 to counter double current distribution to obtain preparations containing a mixture of U-44,590 and U-50,228; and
 b. subjecting said preparations to silica gel chromatography to isolate a pure preparation of U-50,228.

5. A process, according to claim 4, wherein said counter double current distribution is conducted using a solvent system consisting of 1-butanol-water (1:1).

6. A process, according to claim 4, wherein said silica gel chromatography is conducted using a solvent system consisting of ethyl acetate-methanol (6:1 v/v).

7. A process for isolating pure U-50,228 from a preparation containing a mixture of U-50,228 and U-44,590, which comprises:
 a. subjecting a preparation containing a mixture of U-44,590 and U-50,228 to a series of silica gel chromatographies to obtain fractions containing U-44,590 and U-50,228;
 b. acetylating said fractions containing a mixture of U-44,590 and U-50,228 to obtain acetylated U-50,228 free of acetylated U-44,590;
 c. subjecting said acetylated U-50,228 to silica gel chromatography to obtain a pure preparation of acetylated U-50,228; and
 d. subjecting said pure preparation of acetylated U-50,228 to a deacetylation procedure to obtain a deacetylated preparation of U-50,228 which is then subjected to silica gel chromatography to give a pure preparation of U-50,228.

* * * * *

UNITED STATES PATENT AND TRADEMARK OFFICE
CERTIFICATE OF CORRECTION

PATENT NO. : 3,988,314
DATED : October 26, 1976
INVENTOR(S) : Alexander D. Argoudelis and Stephen A. Mizsak It is certified that error appears in the above-identified patent and that said Letters Patent are hereby corrected as shown below:

Column 12, lines 50-53, for " $-CH-\underset{|}{CH}-\underset{|}{CH}-CH-CH_2OH$ " with OH OH above the second and third CH read -- $-CH-\underset{|}{CH}-\underset{|}{CH}-CH-CH_2OR'$ -- with OR OR above the second and third CH.

Signed and Sealed this

First Day of March 1977

[SEAL]

Attest:

RUTH C. MASON
Attesting Officer

C. MARSHALL DANN
Commissioner of Patents and Trademarks